US011272959B2

(12) United States Patent
Biedermann et al.

(10) Patent No.: US 11,272,959 B2
(45) Date of Patent: Mar. 15, 2022

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

(21) Appl. No.: 17/234,148

(22) Filed: Apr. 19, 2021

(65) Prior Publication Data
US 2021/0330362 A1    Oct. 28, 2021

Related U.S. Application Data

(60) Provisional application No. 63/014,509, filed on Apr. 23, 2020.

(30) Foreign Application Priority Data

Apr. 23, 2020  (EP) ..................... 20171052

(51) Int. Cl.
*A61B 17/70* (2006.01)
*A61B 17/86* (2006.01)
(Continued)

(52) U.S. Cl.
CPC ...... *A61B 17/7032* (2013.01); *A61B 17/7037* (2013.01); *A61B 17/8685* (2013.01);
(Continued)

(58) Field of Classification Search
CPC .............. A61B 17/704; A61B 17/7037; A61B 17/7035; A61B 17/7034; A61B 17/7032
See application file for complete search history.

(56) References Cited

U.S. PATENT DOCUMENTS 7,708,762 B2   5/2010  McCarthy et al.
7,722,649 B2   5/2010  Biedermann et al.
(Continued)

FOREIGN PATENT DOCUMENTS

EP   1 795 134 A1   6/2007
EP   2 586 391 A1   5/2013
(Continued)

OTHER PUBLICATIONS

Extended European Search Report for Application No. 20171052.2, dated Oct. 12, 2020, 11 pages.
(Continued)

*Primary Examiner* — Julianna N Harvey
(74) *Attorney, Agent, or Firm* — Lewis Roca Rothgerber Christie LLP

(57) ABSTRACT

A bone anchoring device for anchoring a rod to a bone or vertebra includes a receiving part having two legs defining a channel for the rod, and a rod receiving member positionable in the channel, the rod receiving member including an upper surface and a lower surface defining a longitudinally extending passage for receiving the rod and respectively configured to restrict upward and downward movement of a rod received in the passage. The rod receiving member is adjustable from a first configuration where the passage is unobstructed and the rod is movable longitudinally through the passage, to a second configuration where an engagement surface attached to other portions of the rod receiving member is advanced axially into the passage to engage the rod while a rotational orientation of the engagement surface remains constant to restrict movement of the rod in the passage.

23 Claims, 12 Drawing Sheets

(51) Int. Cl.
  *A61B 17/56* (2006.01)
  *A61B 17/00* (2006.01)
(52) U.S. Cl.
  CPC ............ *A61B 2017/00862* (2013.01); *A61B 2017/564* (2013.01)

(56) References Cited

U.S. PATENT DOCUMENTS

| | | | |
|---|---|---|---|
| 7,794,481 B2 | 9/2010 | Molz, IV et al. | |
| 8,105,364 B2 | 1/2012 | McCarthy et al. | |
| 9,393,047 B2 | 7/2016 | Jackson et al. | |
| 2004/0215190 A1* | 10/2004 | Nguyen | A61B 17/704 606/86 A |
| 2006/0229615 A1* | 10/2006 | Abdou | A61B 17/7037 606/256 |
| 2008/0161859 A1* | 7/2008 | Nilsson | A61B 17/7037 606/266 |
| 2009/0264931 A1* | 10/2009 | Miller | A61B 17/704 606/251 |
| 2012/0143255 A1* | 6/2012 | Jackson | A61B 17/7004 606/259 |
| 2013/0231707 A1* | 9/2013 | Juchno | A61B 17/7037 606/305 |
| 2014/0142634 A1* | 5/2014 | Schlaepfer | A61B 17/7037 606/278 |
| 2016/0354118 A1* | 12/2016 | Belliard | A61B 17/704 |

FOREIGN PATENT DOCUMENTS

| | | |
|---|---|---|
| EP | 2 732 782 A1 | 5/2014 |
| EP | 2 829 243 A1 | 1/2015 |
| EP | 3 100 693 A1 | 12/2016 |
| WO | WO 2006/089292 A2 | 8/2006 |

OTHER PUBLICATIONS

Medtronic, "Shilla Growth Guidance System," Product Information, 20 pages, 2012.

* cited by examiner

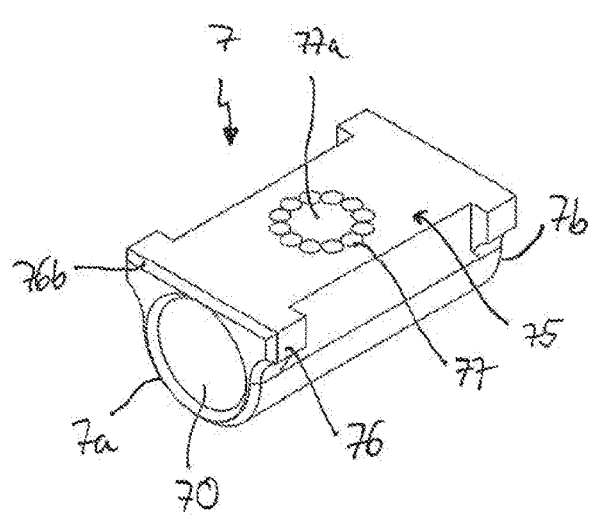
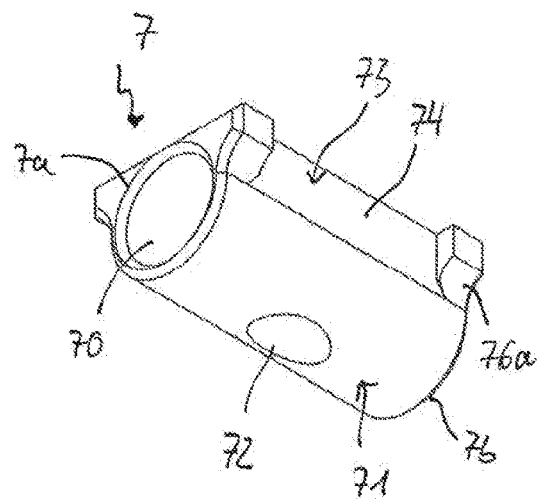
Fig. 12              Fig. 13
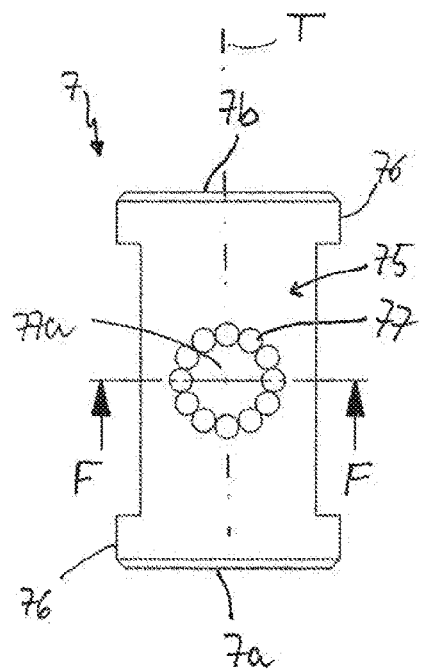
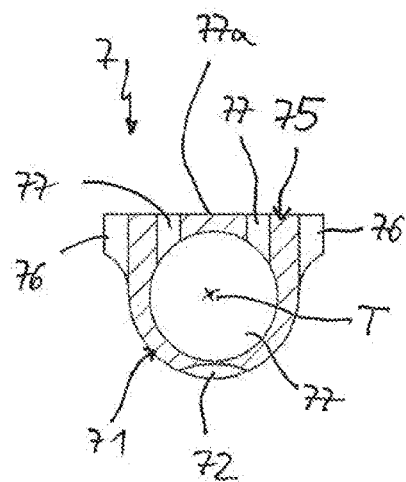
Fig. 14              Fig. 15

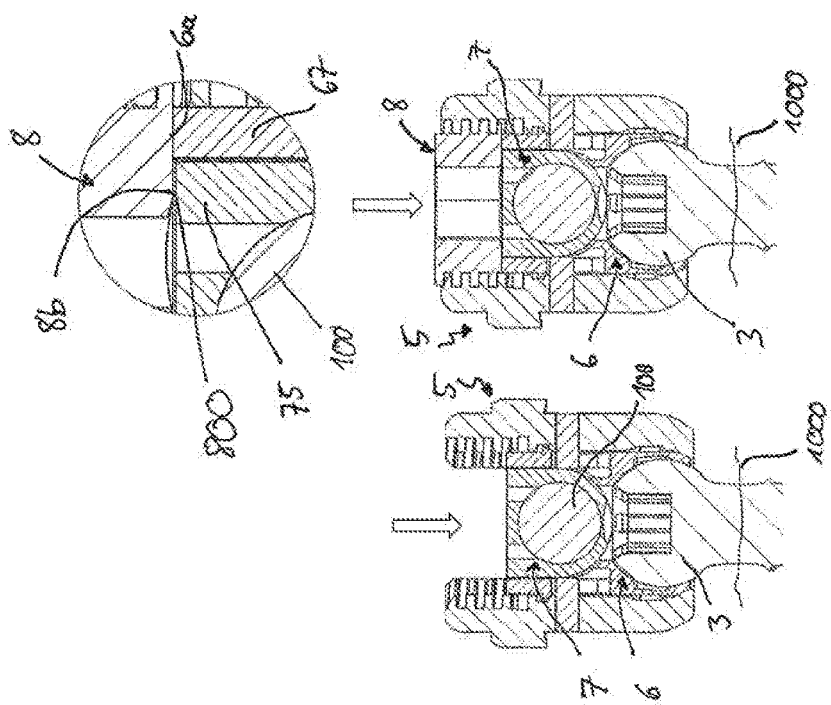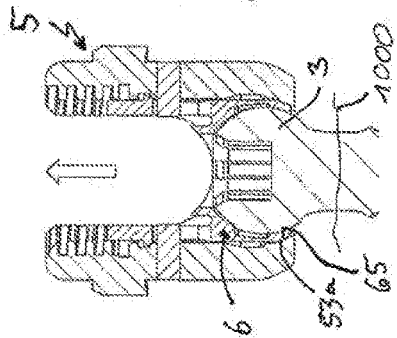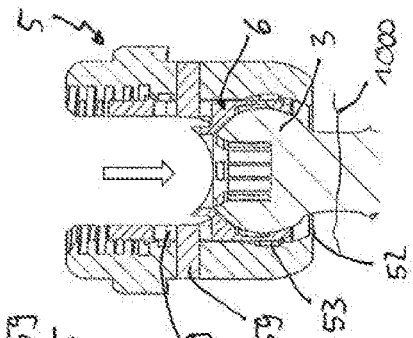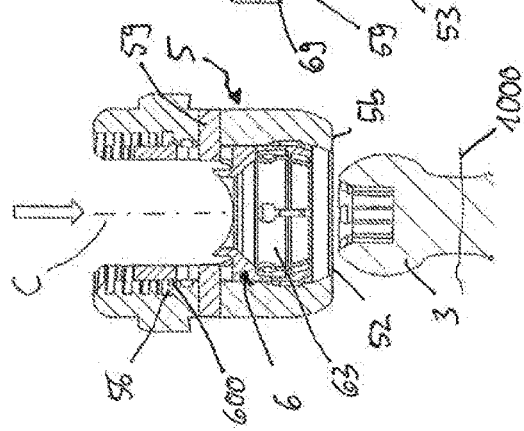

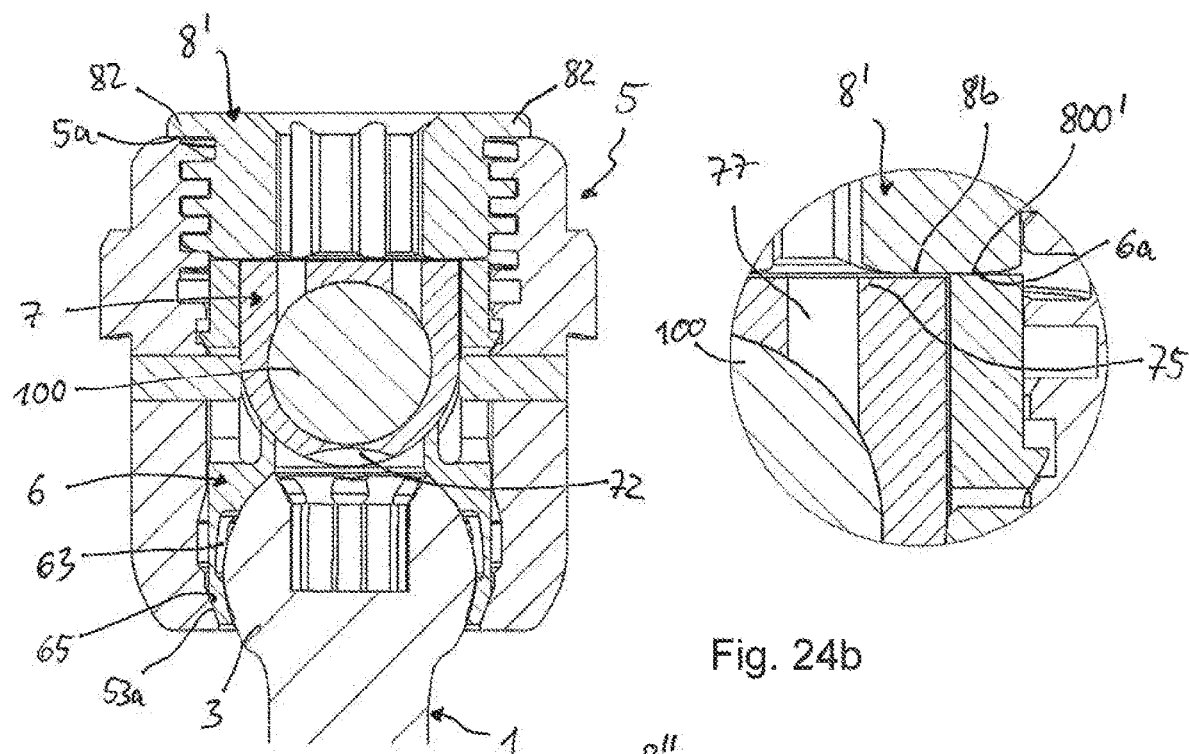
Fig. 24a
Fig. 24b
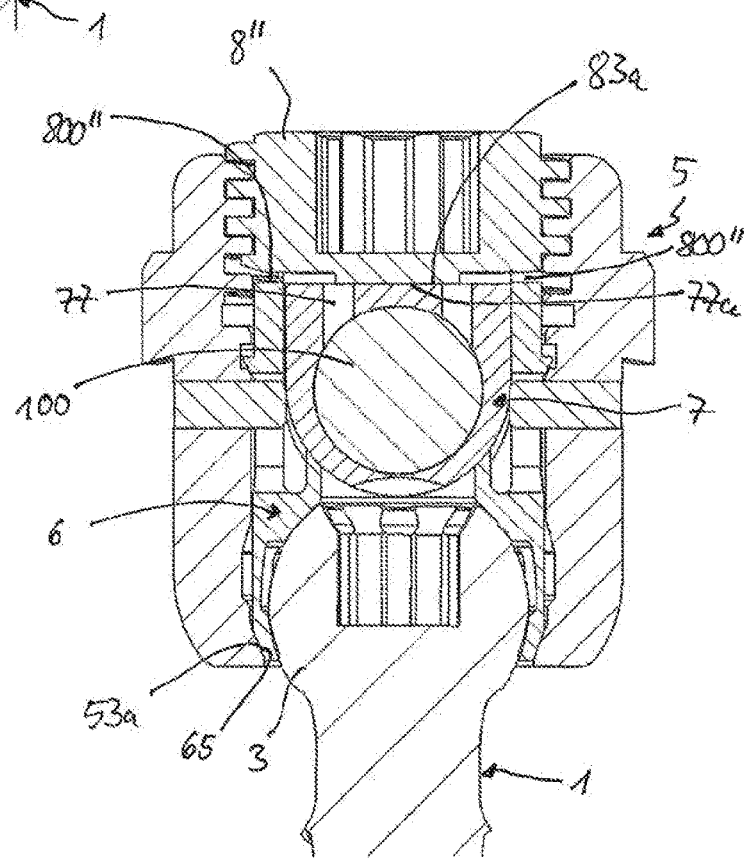
Fig. 25

BONE ANCHORING DEVICE

CROSS-REFERENCE TO RELATED APPLICATION(S)

The present application claims priority to and the benefit of U.S. Provisional Patent Application No. 63/014,509, filed Apr. 23, 2020, the contents of which are hereby incorporated by reference in their entirety, and claims priority from European Patent Application EP 20 171 052.2, filed Apr. 23, 2020, the contents of which are hereby incorporated by reference in their entirety.

BACKGROUND

Field

The application relates to a bone anchoring device that can be used together with a stabilization rod in multiple ways. The bone anchoring device is particularly applicable to the correction of deformities of the spine, more particularly of the pediatric spine. The bone anchoring device can also be useful in degenerative spinal surgery, in particular in dynamic stabilization or hybrid constructs.

Description of Related Art

For the treatment of early onset scoliosis of the pediatric spine, it is known to use growing rods. These are spinal implants fixed above and below the abnormally curved portion of the spine to correct the curvature in a first step to some extent. Thereafter, the rods are prolonged in further correction surgeries to adapt them to the growth of the spine.

Systems, devices and methods for stabilization of the spinal column, in particular for treating infantile or juvenile scoliosis are known, for example, from U.S. Pat. No. 7,708,762 B2. A system described there includes an elongate support member and a plurality of anchor members configured for anchoring to respective vertebrae. A first of the anchor members is engaged to the elongate support member in a manner that substantially prevents axial movement of the support member relative to the first anchor member, and a second of the anchor members is engaged to the support member in a manner that allows substantially unconstrained axial movement of the support member relative to the second anchor member. With the system and device, the number and/or frequency of adjustments of the stabilization system to accommodate for continued growth of the patients spinal column, particularly in pediatric patients, can be reduced.

A dynamic stabilization device for bones, in particular for vertebrae, is known from U.S. Pat. No. 7,722,649 B2, which includes two bone anchoring elements and a rigid rod connecting the bone anchoring elements. An elastic element is inserted between the two bone anchoring elements. At least one of the bone anchoring elements is fixedly connected to the rod to prevent translational movement of the rod relative to it. Another bone anchoring element can be connected to the rod in a manner such that it is displaceable in the direction of a longitudinal axis of the rod.

SUMMARY

It is an object of the invention to provide a bone anchoring device and a kit including a bone anchoring device and at least two fixation members that provide an improved or alternative way of treating spinal deformities, and more particularly deformities in the pediatric or juvenile spine, or in degenerative spinal surgery, in particular in dynamic stabilization or hybrid construct applications.

According to an embodiment, the bone anchoring device includes a receiving part being fixedly or pivotably connectable to a shank that is configured to be anchored in bone or in a vertebra. The receiving part has a recess forming two free legs that provide a channel for inserting the rod. A rod receiving member having a passage that extends longitudinally for receiving the rod is configured to be arranged in the channel. The rod receiving member is configured to assume a first configuration in which the rod is displaceable or movable in the passage in the longitudinal direction and a second configuration in which the rod is restrained from being displaced or moved in the passage.

The bone anchoring device can be employed as a bone anchoring device that is fixed to the rod, and/or as a bone anchoring device that is slidable with respect to the rod to permit a positional change of the bone anchoring device relative to the rod when implanted. Thus, the bone anchoring device can be used as a growing construct that allows the spine to grow while correcting a scoliotic deformity. Whether a fixed or a slidable connection is established can be easily selected by using an appropriate fixation member.

According to a further aspect, the bone anchoring device is a polyaxial bone anchoring device. This means that the receiving part is pivotably coupled to a head provided at an end of the shank, and a pressure element is arranged in the receiving part that is configured to exert pressure onto the head. With a first fixation member, it is possible to clamp or substantially lock the head while the rod is still freely displaceable within the rod receiving member. A second fixation member is configured to be insertable into the receiving part in a limited manner, so that the head is still freely pivotable and the rod is displaceable in the rod receiving member. A third fixation member is configured to exert pressure only onto the rod receiving member, so as to finally lock the rod and also the head.

Thus, the bone anchoring device according to embodiments of the invention provides a modular system that permits different locking configurations of the head and/or the rod by selecting one from among a plurality of fixation members that are insertable into the rod channel of the receiving part. By means of this, the bone anchoring device can be used with a suitable fixation member as either an anchoring device which is fixed to the rod or an anchoring device that is displaceable relative to the rod. In particular for the correction of scoliosis, especially in children or juveniles, a stabilization system including the rod and several bone anchoring devices can grow with a growing spine, since the rod can be kept displaceable relative to certain bone anchoring devices of a stabilization system.

The bone anchoring device may be a bottom loading bone anchoring device in which the head of the bone anchoring element is inserted through a bottom end of the receiving part. In some embodiments, the bone anchoring device may instead or also be a top loading bone anchoring device in which the anchoring element is inserted from a top end of the receiving part.

According to still further embodiments, a rod receiving member is provided that has a sleeve-like portion for receiving a rod and a deformable portion on one side which is configured to be engaged by a fixation member of a bone anchoring device, such that when the rod receiving member with inserted rod is placed into a receiving part of a bone anchoring device, the rod receiving member can assume a first configuration in which the rod is slidable or otherwise axially displaceable in the rod receiving member, and a second configuration in which the rod is axially fixed when pressure is exerted onto the deformable portion of the rod receiving member by the fixation member. The rod receiving member may be made of a material that exhibits flexibility, such as a plastic material, for example, a polymer such as polyether ether ketone (PEEK).

BRIEF DESCRIPTION OF THE DRAWINGS

Further features and advantages of the invention will become apparent from the description of embodiments by means of the accompanying drawings. In the drawings:

FIG. 12 shows a perspective view from a top of a rod receiving member of the bone anchoring device of FIGS. 1 to 3.

FIG. 13 shows a perspective view from a bottom of the rod receiving member of FIG. 12.

FIG. 14 shows a top view of the rod receiving member of FIGS. 12 and 13.

FIG. 15 shows a cross-sectional view of the rod receiving member of FIGS. 12 to 14, the cross-section taken along line F-F in FIG. 14.

FIGS. 16a to 16e show steps of assembling the bone anchoring device of FIGS. 1 to 3.

FIG. 24a shows a cross-sectional view of the bone anchoring device of FIGS. 1 to 3 with the second fixation member shown in FIGS. 20 and 21, in a configuration where the rod is displaceable in the receiving part and the head is pivotable.

FIG. 24b shows a detail of FIG. 24a.

FIG. 25 shows a cross-sectional view of the bone anchoring device of FIGS. 1 to 3 with the third fixation member shown in FIGS. 22 and 23, in a configuration where the head is locked and the rod is fixed.

DETAILED DESCRIPTION

Figures 1, 2:
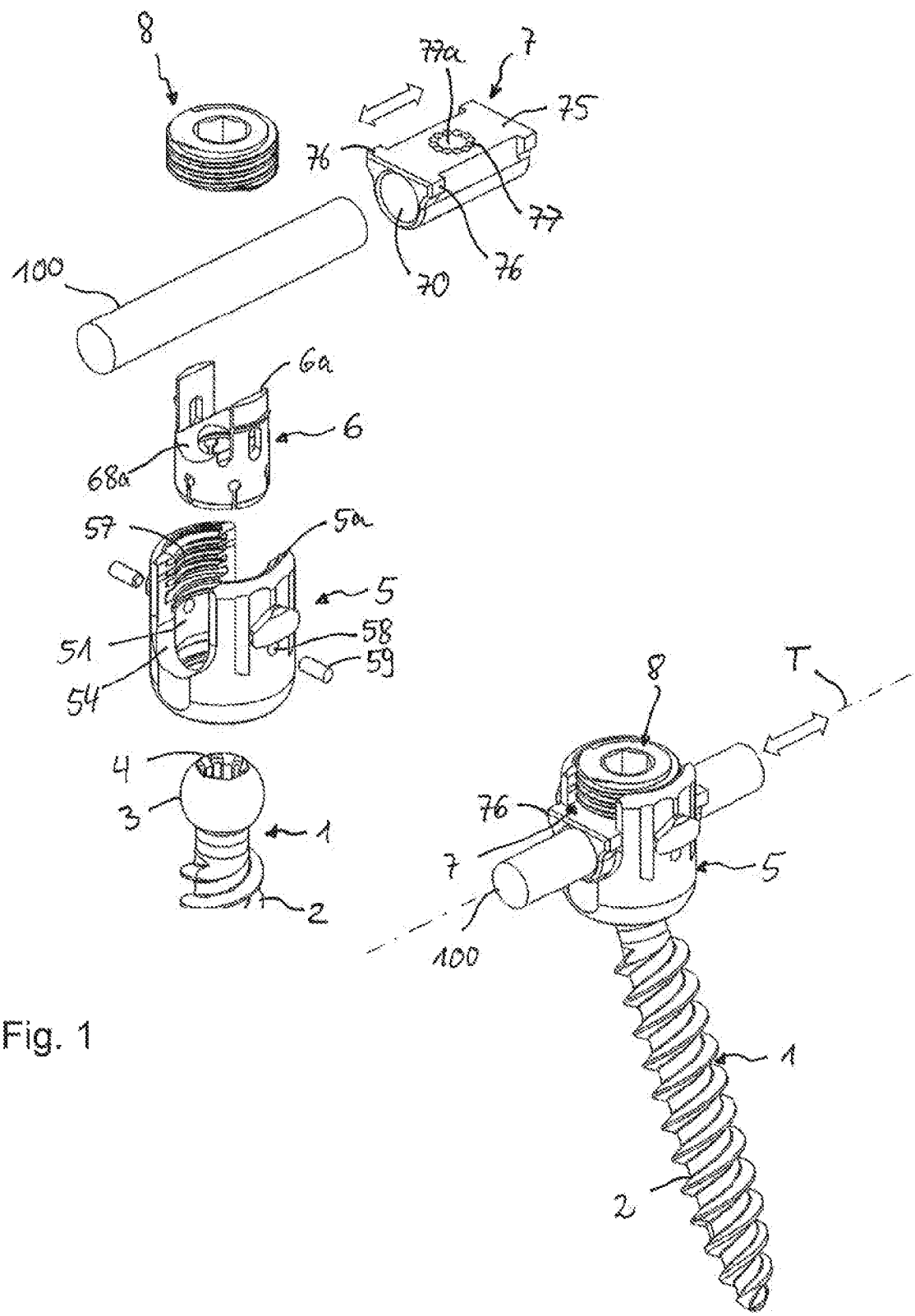
FIG. 1 shows an exploded perspective view of a bone anchoring device according to an embodiment of the invention.
FIG. 2 shows a perspective view of the bone anchoring device of FIG. 1 in an assembled state.
Figure 3:
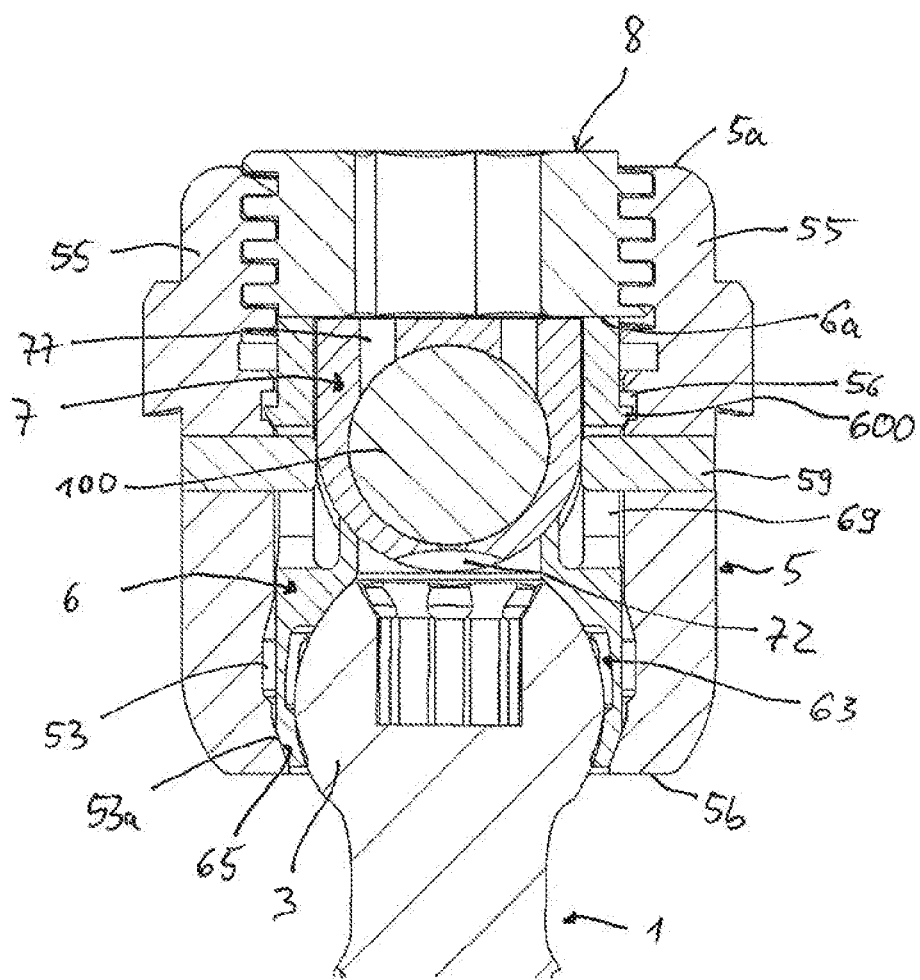
FIG. 3 shows a cross-sectional view of the bone anchoring device of FIGS. 1 and 2, wherein the cross-section is taken in a plane perpendicular to a longitudinal axis of a rod channel of a receiving part of the bone anchoring device and extending through a center of the legs of the receiving part.
Figure 4:
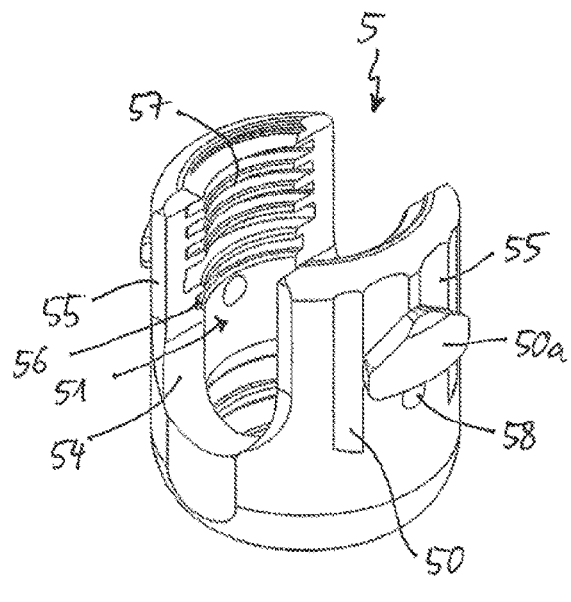
FIG. 4 shows a perspective view from a top of the receiving part of the bone anchoring device of FIGS. 1 to 3.
Figure 5:
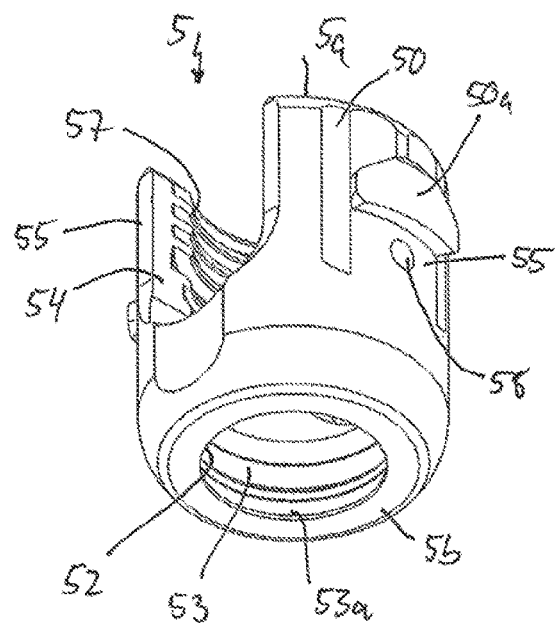
FIG. 5 shows a perspective view from a bottom of the receiving part of FIG. 4.
Figure 6:
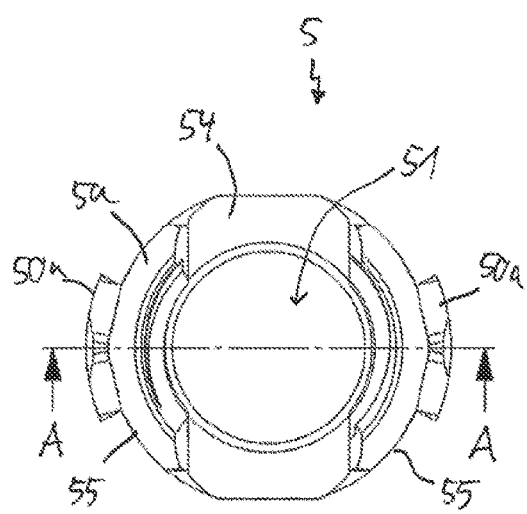
FIG. 6 shows a top view of the receiving part of FIGS. 4 and 5.
Figure 7:
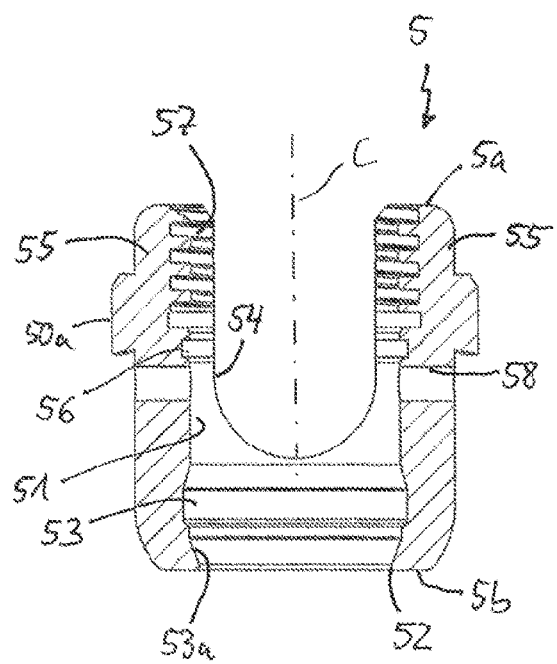
FIG. 7 shows a cross-sectional view of the receiving part of FIGS. 4 to 6, the cross-section taken along line A-A in FIG. 6.
Figure 8:
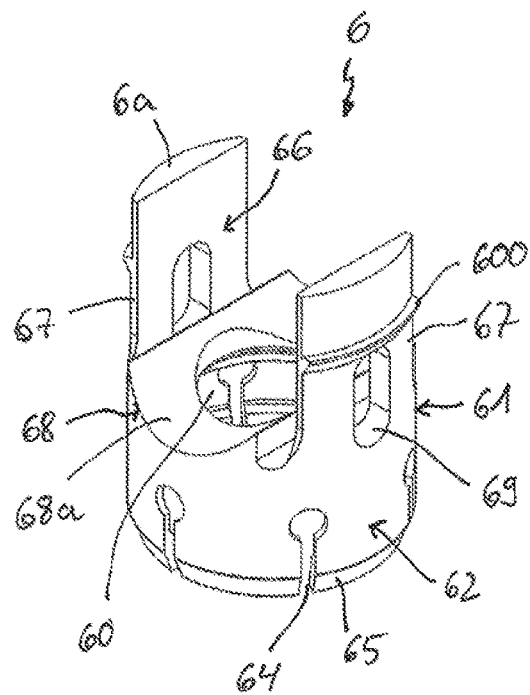
FIG. 8 shows a perspective view from a top of a pressure element of the bone anchoring device of FIGS. 1 to 3.
Figure 9:
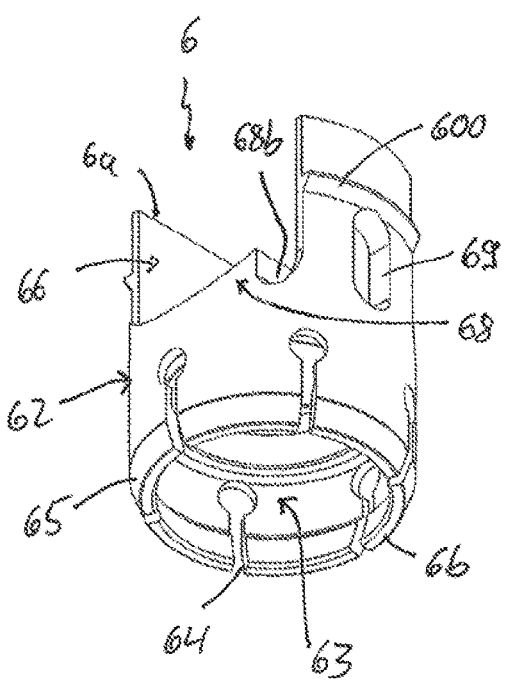
FIG. 9 shows a perspective view from a bottom of the pressure element of FIG. 8.
Figure 10:
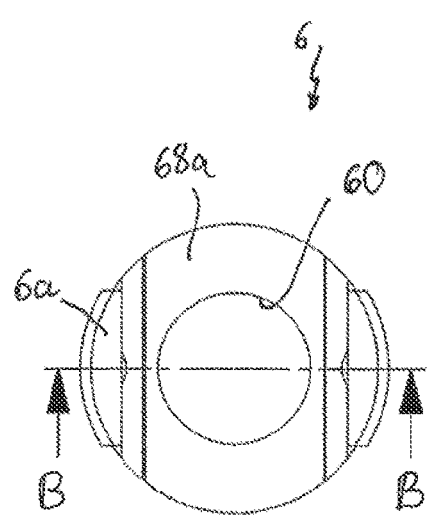
FIG. 10 shows a top view of the pressure element of FIGS. 8 and 9.
Figure 11:
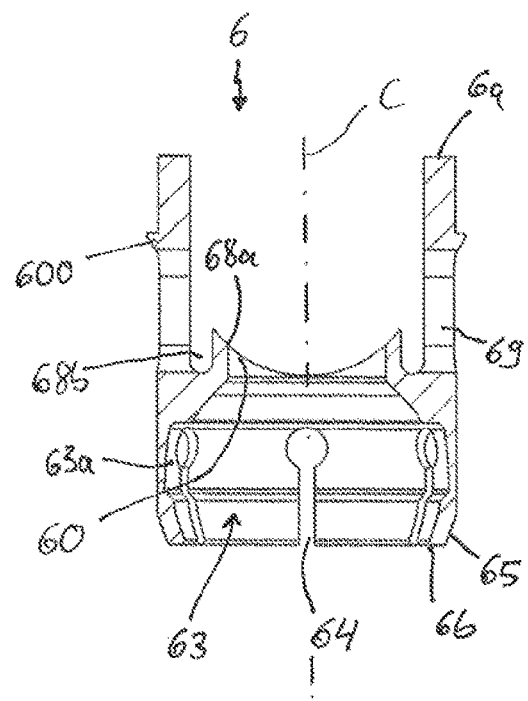
FIG. 11 shows a cross-sectional view of the pressure element of FIGS. 8 to 10, the cross-section taken along line B-B in FIG. 10.

Referring to FIGS. 1 to 3, a bone anchoring device according to a first embodiment is a polyaxial bone anchoring device. The bone anchoring device includes a bone anchoring element 1 having a shank 2 with a threaded portion and a head 3. The head 3 has a spherically shaped outer surface portion and, on its side opposite to the shank 2, a recess 4 for engagement with a tool. A receiving part 5 is further provided for coupling the bone anchoring element 1 to a rod 100. In the receiving part 5, a pressure element 6 can be arranged to exert pressure onto the head 3 of the bone anchoring element 1.

Additionally, the bone anchoring device includes a rod receiving member 7 that is configured to receive the rod 100. The rod receiving member 7 is further configured to be arranged in the receiving part 5. Moreover, the bone anchoring device includes a fixation member 8 that is configured to cooperate with the receiving part 5 to secure the rod receiving member 7 with an inserted rod 100 in the receiving part.

The rod 100 may be a cylindrical straight rod that is configured to stabilize bone parts or vertebrae connected through the rod. In particular, the rod 100 is preferably a stiff or inelastic rod, and more specifically the rod is substantially free from flexible or elastic characteristics when implanted into a patient's body. Preferably, the surface of the rod 100 is smooth at least to an extent such that the rod 100 can slide within the rod receiving member 7. It shall be noted that the rod is not limited to a straight rod as depicted in the embodiment, but shall include any elongate stabilization member that is configured to be displaceably, in particular slidably, receivable in the rod receiving member 7.

Turning now to FIGS. 4 to 7, the receiving part will be described in greater detail. The receiving part 5 has a first or top end 5a and a second or bottom end 5b opposite to the top end 5a. The receiving part may have a substantially cylindrical outer shape, with a central longitudinal axis C extending through the top end 5a and the bottom end 5b. Coaxially with the central axis C, a passage 51 is provided that extends from the top end 5a to the bottom end 5b and that forms an opening 52 at the bottom end 5b. At a distance from the top end 5a, the passage 51 widens into an accommodation space 53 that is configured to receive the head 3 and at least a portion of the pressure element 6. Adjacent to the opening 52 at the bottom end 5b, the accommodation space 53 narrows towards the opening 52 in a narrowing portion 53a, which may be, for example, a tapered, and more particularly a conical surface that may cooperate with a corresponding portion of the pressure element 6. The width of the opening 52 may be greater than the greatest width of the head 3, so that the head 3 may be inserted from the bottom end 5b into the accommodation space 53. To enable the insertion of the head 3 from the bottom end 5b, the width of the accommodation space 53 is such that the pressure element 6 can expand therein to permit the insertion of the head 3.

The receiving part 5 further has a substantially U-shaped recess 54 starting at the top end 5a and extending in the direction of the bottom end 5b. By means of the U-shaped recess 54, two free legs 55 are formed and define a channel that is open towards the first end 5a for receiving the rod receiving member 7 with inserted rod 100.

On an inner surface of the legs 55, an inner thread 57 is formed, which is in the exemplary embodiment a square thread or another flat thread. A circumferential groove 56 may be provided at the inner wall of the legs 55 at a distance from a bottom of the U-shaped recess 54. The inner groove 56 may provide a stop for restricting an upward movement of the pressure element 6 towards the first end 5a when the pressure element is assembled with the receiving part.

In addition, transverse holes 58 may extend through the legs 55, respectively, in a direction perpendicular to the central axis C and at a position approximately at the center of each of the legs 55 in a circumferential direction. The transverse holes 58 may serve for accommodating pins 59 that extend through the holes 58 into the channel. The pins 59 are configured to engage the pressure element 6 to form a securing device to secure the pressure element 6 against rotation. In addition, the pins 59 may limit an upward movement of the pressure element 6. At the outside of the legs 55, for example, longitudinal recesses 50 and/or attachment projections 50a may be provided for engagement with a tool or instrument.

Referring to FIGS. 8 to 11, the pressure element 6 may be formed as a monolithic part, with a first or upper end 6a and a second or lower end 6b opposite to the upper end 6a. Adjacent to the upper end 6a, the pressure element has a substantially cylindrical first portion 61 that is adapted to be received in the passage 51 of the receiving part 5 and to move therein in an axial direction. Adjacent to the lower end 6b, a second substantially cylindrical portion 62 is formed that is configured to extend at least partially into the accommodation space 53 of the receiving part 5. Further, adjacent to the lower end 6b, a head receiving recess 63 is formed in the second portion 62, which is designed and sized so as to frictionally hold the head 3 of the bone anchoring element 1 therein. To achieve this, the overall shape of the head receiving recess 63 is adapted to the spherical shape of the head 3. A widened cylindrical portion 63a may enhance flexibility of the head receiving recess 63 and may facilitate easier pivoting of the head 3. A plurality of longitudinal slits 64, preferably with widened end portions, extend into the wall of the second portion and render the second portion 62 flexible. Adjacent to the lower end 6b, the outer surface of the second portion 62 includes a narrowing portion 65, preferably a tapered and more preferably a conically-tapered portion that is configured to cooperate with the narrowing portion 53a of the accommodation space 53. By means of the cooperating surfaces 65, 53a of the pressure element 6 and the receiving part 5, respectively, the flexible second portion 62 of the pressure element 6 can be compressed to clamp or lock the head 3 therein.

Adjacent to the upper end 6a, a substantially U-shaped recess 66 forms two open legs 67 that preferably have substantially flat inner walls. The substantially U-shaped recess 66 has an elevated base 68 with a concavely-formed cylindrical upper support surface 68a having a cylinder axis extending transverse to the central axis C. The support surface 68a is configured to receive a portion of the rod receiving member 7 thereon. The support surface 68a lies at such a height with respect to the upper end 6a of the pressure element 6 that, when the rod receiving member 7 rests on the base, the upper end 6a of the pressure element, and more specifically of the legs 67, project above the upper surface of the rod receiving member 7. By means of the elevated base 68, two grooves 68b are formed between the right and the left side of the elevated base 68 and the legs 67.

The pressure element 6 also includes a coaxial bore 60 that serves for accessing the recess 4 of the head 3 with a tool. In addition, at approximately the center of each of the legs 67 in a circumferential direction, an axially elongate hole 69 is provided that is configured to be engaged by the pins 59. The cooperation between the pins 59 and the elongate holes 69 prevent rotation between the pressure element 6 and the receiving part 5. Furthermore, the pins 59 form a stop against an upward movement of the pressure element 6 when the head 3 is inserted through the lower opening 52 of the receiving part into the recess 63 of the pressure element 6. Above the elongate recesses 69, circumferentially extending projections 600 with a substantially flat upper surface may be provided that are configured to engage the groove 56 of the receiving part 5, to avoid loss of the pressure element 6 when it is pre-assembled to the receiving part 5.

The bone anchoring element, the receiving part, and the pressure element, as well as the rod and the fixation member may be made of the same or of different materials, preferably of bio-compatible materials such as titanium or stainless steel, or of a bio-compatible alloy, such as NiTi alloys, for example Nitinol, or of a bio-compatible plastic material, for example, polyether ether ketone (PEEK).

Referring further to FIGS. 12 to 15, the rod receiving member 7 is formed as a sleeve-like part with a first end 7a and an opposite end 7b, and an elongate passage 70 extending from the first end 7a to the second end 7b. The passage defines a longitudinal axis T. The cross-section of the passage 70 may be adapted to the cross-section of the rod 100. In the embodiment, the passage is cylindrical, so that the longitudinal axis is the cylinder axis and has a size such that the rod 100 can be displaced therein along the longitudinal axis, and more specifically can slide within the passage 70. In greater detail, the passage 70 may have a cross-section such that the rod 100 can be displaced in the passage along the longitudinal axis T without getting jammed. Also, the size is such that the rod receiving member 7 can be slightly deformed to clamp the rod in the passage, as explained below. The length of the rod receiving member 7 in the direction of the longitudinal axis T is such that when the rod receiving member 7 is placed into the receiving part, the first end 7a and the second end 7b extend out of the U-shaped recess 54 in the axial direction of the channel axis of the U-shaped recess 54.

The outer shape of the rod receiving member 7 is, in a lower portion 71, i.e., a portion configured to be positioned closer to the bottom end 5b of the receiving part in the assembled state, substantially cylinder segment-shaped. The lower portion 71 is configured to rest on the support surface 68a of the pressure element 6. At the center of the lower portion 71, between the ends 7a, 7b, a spherically-shaped recess 72 may be formed that permits a portion of the head 3 to extend therein when the head 3 pivots in the head receiving recess 63 of the pressure element 6. More specifically, a radius of the recess 72 matches a radius of the head receiving recess 63, so that when the head 3 pivots, the head can easily enter the recess 72. An upper portion 73 of the rod receiving member 7 includes two substantially parallel sidewalls 74 and a top wall 75 extending substantially perpendicular to the sidewalls 74. Hence, an outer contour at a center of the rod receiving member 7 is substantially U-shaped with a closed top, as depicted in FIG. 15. The sidewalls 74 have a distance from each other and a length such that the rod receiving member 7 fits into the channel between the legs 67 of the pressure element 6. Moreover, a height of the rod receiving member 7 transverse to the longitudinal axis T is such that the upper surface of the top wall 75 is located below the upper end 6a of the pressure element 6 when the rod receiving member 7 rests on the support surface 68a of the pressure element 6.

The upper surface of the top wall 75 may be substantially flat and is configured to be engaged by a fixation member as described below. Moreover, at each of the first end 7a and the second end 7b, lateral wings or projections 76 extend on each side of the upper portion 73. Hence, four such wings 76 are formed and the wings are arranged substantially symmetrically with respect to a plane extending through the longitudinal axis T and the center of the top wall 75. An outer contour of the wings 76 may be substantially rectangular with a slanted underside 76a. Furthermore, the wings 76 and the top wall 75 may have a bevel 76b at each of the first end 7a and at the second end 7b, respectively.

The top wall 75 is flexible to some extent. In greater detail, the top wall 75 is configured to be compressed or deformed in a direction towards the passage 70 when pressure is exerted thereon. More specifically, the top wall 75 is also configured to re-assume its non-compressed or undeformed state once the pressure is relieved. To render the top wall 75 at least partially flexible, a plurality of through-holes 77 are provided that extend from the upper surface of the top wall 75 into the passage 70. The axis of the through-holes 77 may be perpendicular to the longitudinal axis T. In the embodiment, the through-holes 77 are arranged in a circle around the center of the top wall 75. By means of the through-holes 77, a weakening of the top wall 75 is achieved. As a result, an area 77a encircled by the through-holes 77 is configured to be engaged by a portion of a fixation member and is configured to be deformed towards the passage 70 when the fixation member exerts pressure thereon. As a result, an inserted rod 100 is fixed at a particular axial position relative to the rod receiving member 7. When the pressure is relieved, the top surface 75 may assume the original non-deformed shape.

To accomplish these characteristics, the rod receiving member 7, and more specifically at least the upper portion 73 including the top wall 75, is made of a material that exhibits sufficient flexibility and/or elasticity. For example, the rod receiving member 7 can be made at least partially or fully of a bio-compatible plastic material, such as PEEK. Other materials, such as a metal or metal alloy with enhanced elastic or super-elastic characteristics, such as β-titanium or super-elastic NiTi alloy can also be used.

Figure 18:
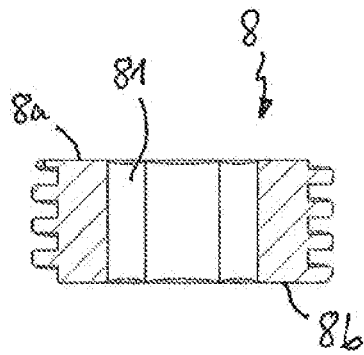
FIGS. 18 and 19 show a cross-sectional view and a top view, respectively, of a first fixation member, the cross-section taken along line G-G in FIG. 19.
Figure 19:
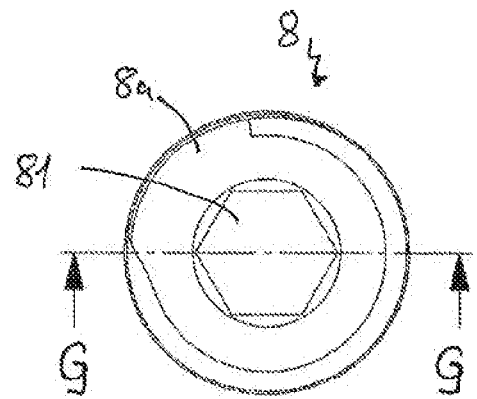

Referring again to FIGS. 1 to 3, and further to FIGS. 18 and 19, the fixation member 8 in this embodiment is formed as a set screw with a tool engagement recess 81, for example a polygonal recess, that may extend fully through the fixation member 8 from an upper side 8a to a lower side 8b. Moreover, the lower side 8b is configured to press onto the upper end 6a of the pressure element but not onto the inserted rod receiving member 7. Preferably, the lower side is substantially flat.

In use, referring to FIGS. 16a to 16e, the receiving part 5 may be preassembled with the pressure element 6 that is held in the receiving part via the pins 59. The receiving part 5 with the pressure element 6 may then be coupled to the bone anchoring element 1 by inserting the head 3 through the opening 52 into the head receiving recess 63 of the pressure element 6. In a first alternative of use, the bone anchoring element has already been inserted into a bone part of vertebra 1000 prior to coupling the receiving part thereto, as shown in FIG. 16a. Alternatively, the bone anchoring element 1 can be coupled to the receiving part first, and thereafter implanted into the bone or vertebra. When the head 3 enters into the head receiving recess 63, the pressure element 6 is moved upwards in the passage 51 until further upward movement is limited by the pins 59. The flexible second portion 62 of the pressure element 6 expands in the accommodation space 53 and snaps onto the head 3 as shown in FIG. 16b. Thereafter, the receiving part is pulled upward relative to the head and the pressure element so that the cooperating surfaces 53a of the receiving part 5 and 65 of the pressure element 6 engage to preliminarily hold the head 3 in the receiving part 5 in a pivotable manner. This step is shown in FIG. 16c.

To connect two bone anchoring devices once inserted into bone parts or vertebrae, the rod 100 with the rod receiving member 7 mounted thereon is inserted into the U-shaped recess 54 of the receiving part 5, as depicted in FIG. 16d. The rod 100 may have at least two or more rod receiving members 7 mounted thereon, which can be displaced along the rod 100 so that they have a distance from each other that corresponds to the distance between the receiving parts 5 into which they are intended to be inserted. When the rod receiving member 7 with inserted rod 100 has been placed into the channel of the receiving part 5 as shown in FIG. 16d, the wings 76 project in a direction perpendicular to the longitudinal axis T out of the recess 54, as best seen in FIG. 2. The distance between the wings 76 in the axial direction is such that the legs 55 of the receiving part are held with little or almost no play between the wings 76. By means of this, the rod receiving member 7 is restrained from moving relative to its corresponding receiving part in the direction of the axis T.

Finally, as shown in FIG. 16e, the fixation member 8 is inserted and tightened until its lower surface 8b presses onto the upper end 6a of the pressure element 6. Since the surface of the top wall 75 of the rod receiving member 7 is located below the upper end 6a of the pressure element 6, there is a gap 800 between the surface of the top wall 75 of the rod receiving member 7 and the lower surface 8b of the fixation member, as depicted in the enlarged portion of FIG. 16e. Tightening the fixation member 8 moves the pressure element 6 deeper into the narrowing portion 53a, thereby compressing the flexible portion 62 of the pressure element 6 around the head 3 so that the head 3 is locked. The locking of the head can be carried out in various pivotal positions of the head. At the same time, the rod 100 remains freely movable.

Figure 17:
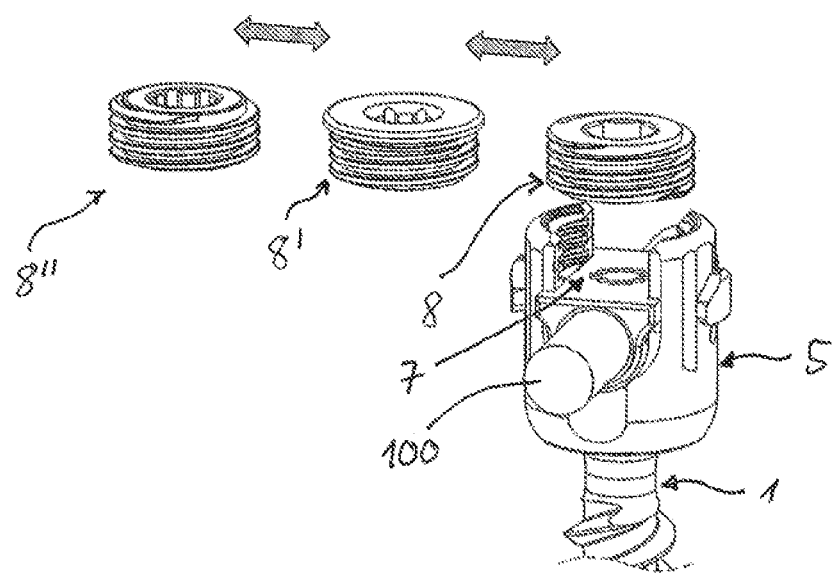
FIG. 17 shows a perspective view of a modular system including the bone anchoring device of FIGS. 1 to 3 and exchangeable fixation members.

The bone anchoring device may include, instead or additionally to the fixation member 8, one or more different fixation members 8', 8". As shown in FIG. 17, the fixation member 8 may be a first fixation member, and a second fixation member 8' and a third fixation member 8" may be provided that can be interchangeably used with the first fixation member 8. The fixation members 8, 8', 8" may differ with respect to their function. Thus, the bone anchoring device as described in FIGS. 1 to 16*e* with at least one further fixation member 8', 8" forms a modular system which permits the selection of a suitable fixation member to accomplish a certain function of the bone anchoring device.

Figure 20:
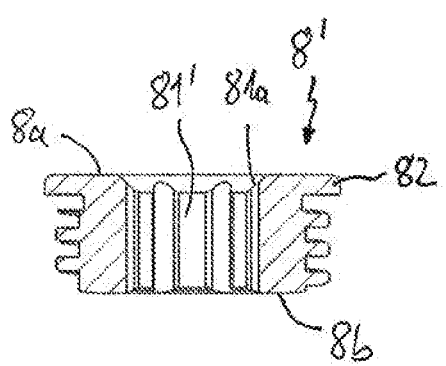
FIGS. 20 and 21 show a cross-sectional view and a top view, respectively, of a second fixation member, the cross-section taken along line H-H in FIG. 21.
Figure 21:
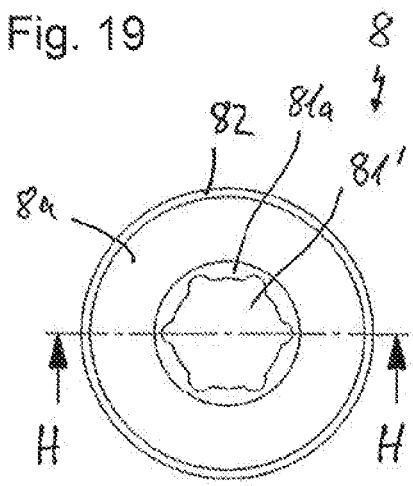
Figure 22:
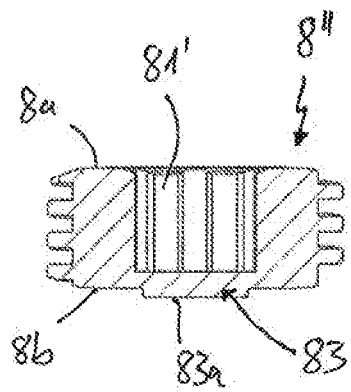
FIGS. 22 and 23 show a cross-sectional view and a top view, respectively, of a third fixation member, the cross-section taken along line I-I in FIG. 23.
Figure 23:
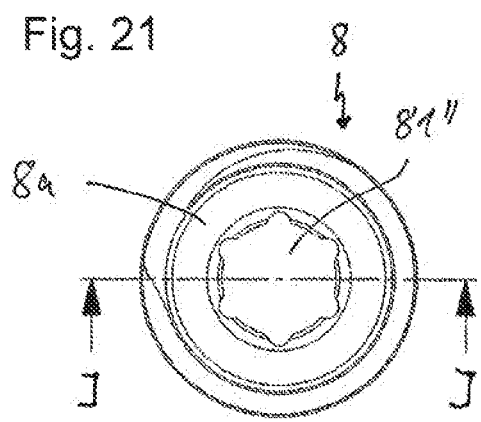

Referring to FIGS. 20 and 21, the second fixation member 8' is formed as a set screw with a tool receiving recess 81' that may extend from the upper end 8*a* to the lower end 8*b* and that may have, for example, a torx-shape. Adjacent to the upper end 8*a*, a circumferentially extending flange 82 is provided that protrudes in a radial direction beyond the outer thread of the set screw. The surface at the lower end 8*b* may be flat. The tool engagement recess 81' may open with a beveled portion 81*a* towards the upper end 8*a*. An axial length of the second fixation member 8' is such that when the second fixation member 8' is inserted between the legs 55 of the receiving part 5 and screwed downward until the flange 82 abuts against the top end 5*a* of the receiving part 5, the lower surface 8*b* does not touch the upper end 6*a* of the pressure element 6, so that there is a gap 800' between the upper end 6*a* of the pressure element 6 and the surface at the lower end 8*b* of the second fixation member 8', as shown in FIGS. 24*a* and 24*b*. Hence, the flange 82 functions as a stop to limit the axial advancement of the second fixation member 8" between the legs 55. As the second fixation member 8' does not press onto the pressure element 6, the receiving part 5 is pivotable around the head 3. Because the second fixation member also does not touch the upper surface of the rod receiving member, the rod 100 is freely displaceable. This opens further possibilities of correction steps in which it may be advantageous to have the receiving part pivotable relative to the shank.

The first and the second fixation members are particularly useful in situations in which the rod shall remain movable relative to the bone anchoring device, such as, for example, in the application of growing rods in the treatment of scoliosis.

The third fixation member 8" includes a substantially cylindrical projection 83 with a free end surface 83*a* at the lower end 8*b*. The projection 83 preferably has a width or diameter slightly smaller than an outer envelope or profile and slightly greater than an inner envelope or profile encircling or defined by the plurality of through-holes 77 in the surface of the top wall 75 of the rod receiving member 7. A length of the projection 83 in an axial direction is such that when the third fixation member 8" is inserted between the legs 55 of the receiving part and the lower surface 83*a* of the projection 83 engages the surface portion 77*a* inside the plurality of through-holes 77 and compresses the top wall 75 at this portion, there is a gap 800" between the upper end 6*a* of the pressure element and the lower end 8*b* of the third fixation member 8'". In addition, the tool receiving recess 81" preferably extends from the upper end 8*a* to a distance from the lower end 8*b*, so that the free end surface 83*a* of the projection 83 is solid, i.e., without a hole.

In use, as depicted in FIG. 25, when the third fixation member 8" is inserted between the legs 55 and tightened against the top wall 75 of the rod receiving member 7, the top wall 75 is compressed slightly downward, such that the portion inside the through-holes 77 clamps and finally locks the rod 100 within the passage 70 of the rod receiving member 7. At the same time, the shank is also locked as the rod receiving member 7 presses onto the pressure element 6, which locks the head 3.

The third fixation member may be particularly useful for full locking of the rod and the head.

Figures 26, 27:
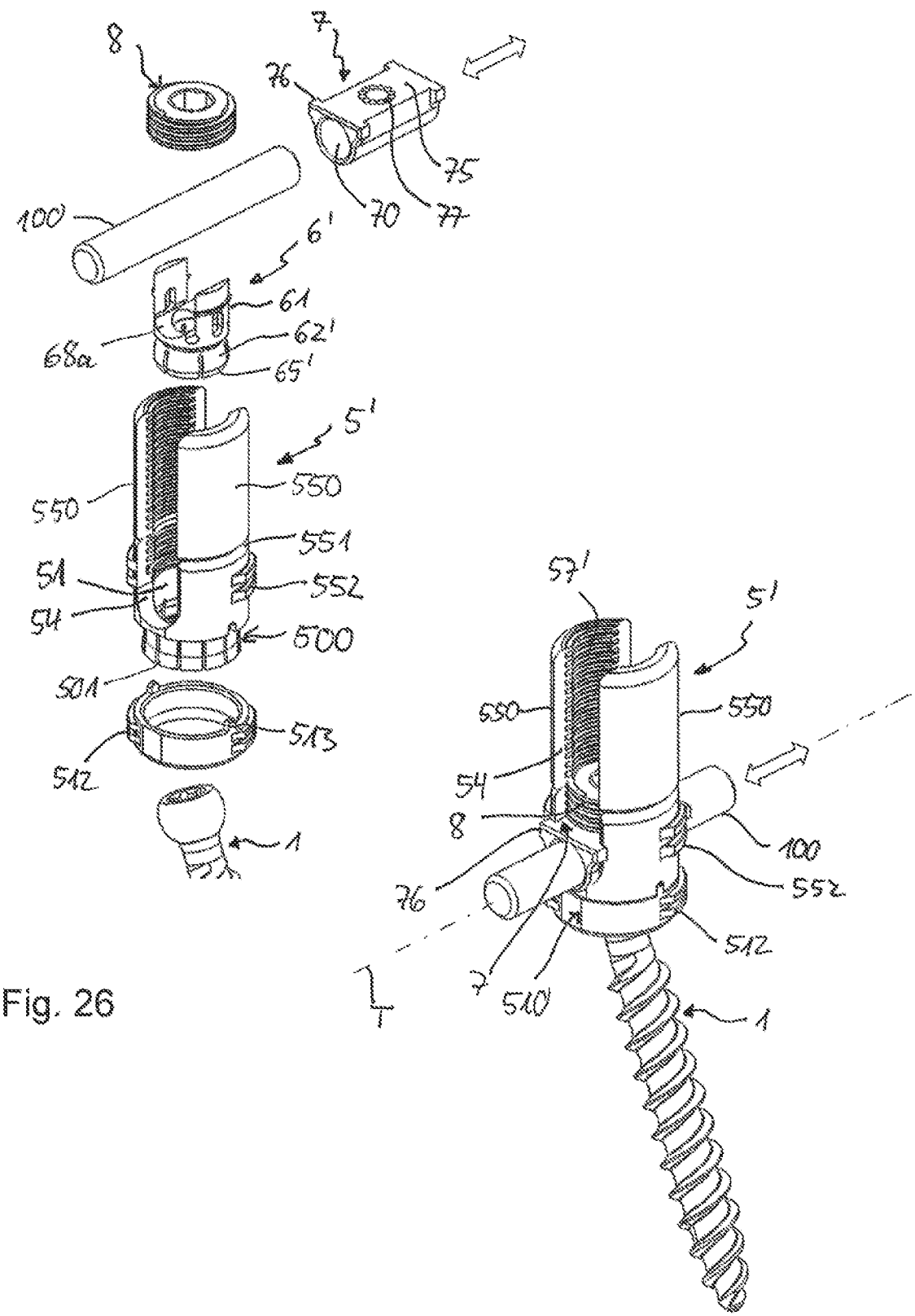
FIG. 26 shows an exploded perspective view of a modified embodiment of the bone anchoring device.
FIG. 27 shows a perspective view of the bone anchoring device of FIG. 26 in an assembled state.
Figure 28:
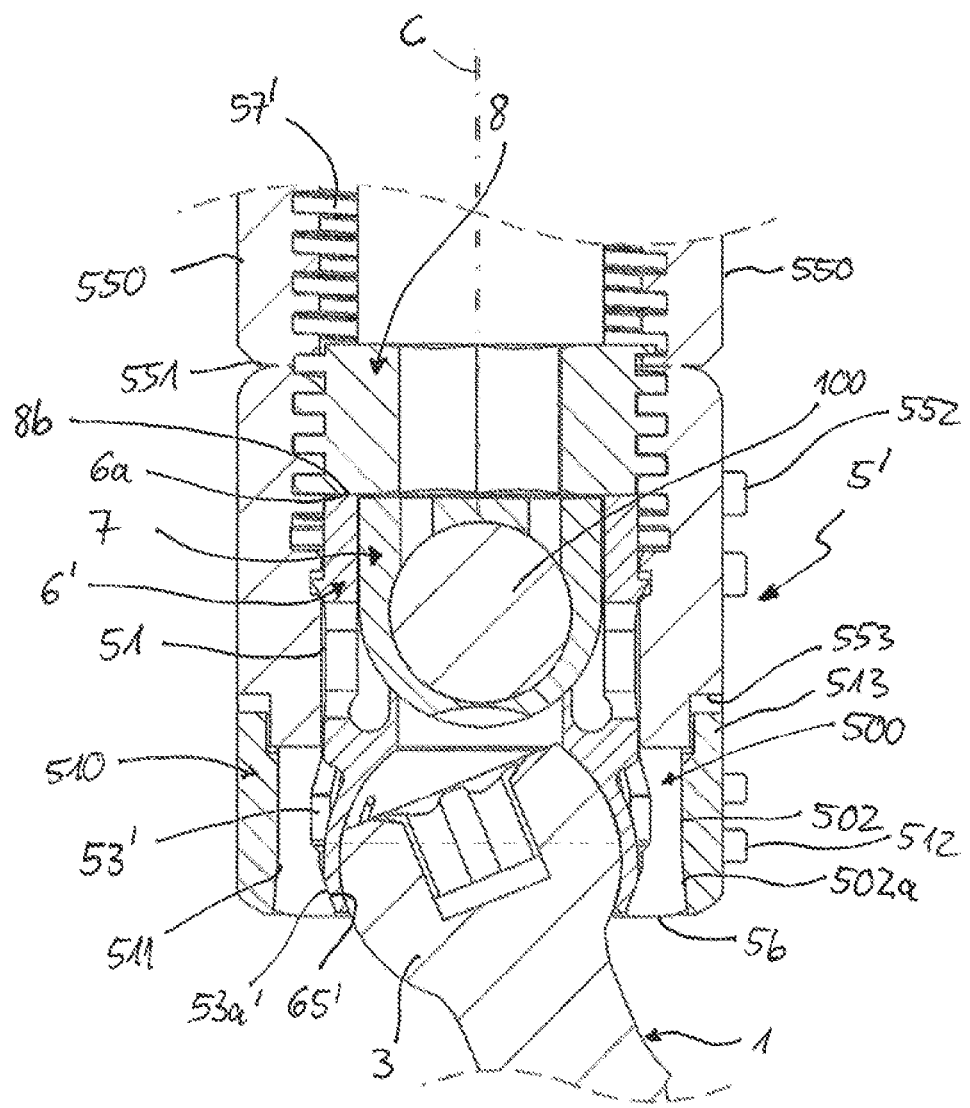
FIG. 28 shows a cross-sectional view of the bone anchoring device of FIGS. 26 and 27, the cross-section taken in a plane perpendicular to a longitudinal axis of a rod channel of a receiving part of the bone anchoring device and extending through a center of the legs of the receiving part.

A modified embodiment of the bone anchoring device will be explained with further reference to FIGS. 26 to 28. The descriptions of parts and portions that are identical or similar to those of the previous embodiments will not be repeated. Specifically, the bone anchoring element 1, the rod 100, the rod receiving member 7, and the fixation members 8, 8" are the same as in the embodiment described before. The receiving part 5' is of the type including an outer locking ring for clamping and locking the head 3 within the receiving part 5'. In greater detail, the receiving part 5' has a lower head receiving portion 500 that includes an accommodation space 53' and a narrowing portion 53*a*', as depicted in FIG. 28. The receiving part 5' further includes an upper rod receiving portion having legs 550. The head receiving portion 500 is flexible, which is achieved by a plurality of slits 501 extending in the axial direction to the bottom end 5*b*. An outer surface 502 of the head receiving portion 500 may be substantially cylindrical with a flared section 502*a*. A locking ring 510 is configured to enclose the head receiving portion 500 circumferentially, and can be moved downwards and upwards, for example, with the aid of an instrument (not shown), to lock and unlock the head 3. The outer surface 502 of the head receiving portion 500 may be recessed with respect to other portions of the receiving part 5', such that an outer surface of the locking ring 510 once it is placed onto the head receiving portion 500 is flush with the outer surface of the upper portion of the receiving part 5'. An inner surface of the locking ring 510 is configured to contact the outer surface 502, 502*a* of the head receiving portion. More specifically, an inner surface 511 of the locking ring 510 may be adapted to the outer surface of the head receiving portion, such that a downward movement of the locking ring 510 away from the top end 5*a* exerts an increasing compression force onto the head receiving portion, thereby locking the head 3 in the head receiving recess 63' of the pressure element 6'. The locking ring 510 further includes an engagement structure 512, for example in the form of circumferential ribs for engagement with the instrument. In addition, the locking ring 510 may include, at its upper end, axially oriented projections 513 that may engage corresponding recesses 553 in the outer surface of the rod receiving upper portion of the receiving part 5', for example, to ensure a proper orientation of the tool engagement structure 512.

The legs 550 are extended, and include a circumferentially extending weakened section 551 forming a break-away portion for breaking away an upper section of the legs 550. The extended legs 550 may be optionally provided and may be particularly suitable for minimally invasive applications. An engagement structure 552 may be provided at an outer surface of the lower portion of the legs 550 that may serve as an abutment for an instrument which moves the locking ring 510 upward and downward while the instrument engages the engagement structure 512.

The upper portion 61 of the pressure element 6' is substantially identical to that of the pressure element 6 of the previous embodiment. The lower portion 62' has an overall cap-shape, with a tapering portion 65' adjacent to the bottom end 6*b*, which is configured to cooperate with the narrowing portion 53*a*' of the head receiving portion. The rod receiving member with inserted rod can be placed between the legs 550 and moved downward until it rests on the support surface 68*a* of the pressure element 6'. Moreover, the extended legs 550 have an inner thread 57', which extends preferably up to their upper free ends so that the fixation member 8, 8" can be screwed downward until it contacts the upper end 6*a* of the pressure element 6' and/or the top wall 75 of the rod receiving member 7.

In use, as depicted in FIG. 28, with the first locking member 8 and the locking ring 510 in the lower position, the head 3 can be clamped while the rod 100 is freely displaceable.

Using the third locking member 8" instead, the rod 100 can also be fixed within the rod receiving member 7. The locking ring 510 is independently movable by the instrument to independently lock and unlock the head.

In this embodiment, the second locking member 8' may also be used after breaking off the extended legs 550.

With this embodiment, various further correction steps may be realized. As the final locking of the head can be achieved via the locking ring with a separate instrument, the final locking of the head can be achieved even if the rod with the rod receiving member and/or the fixation member is not inserted in the channel.

Figures 29, 30:
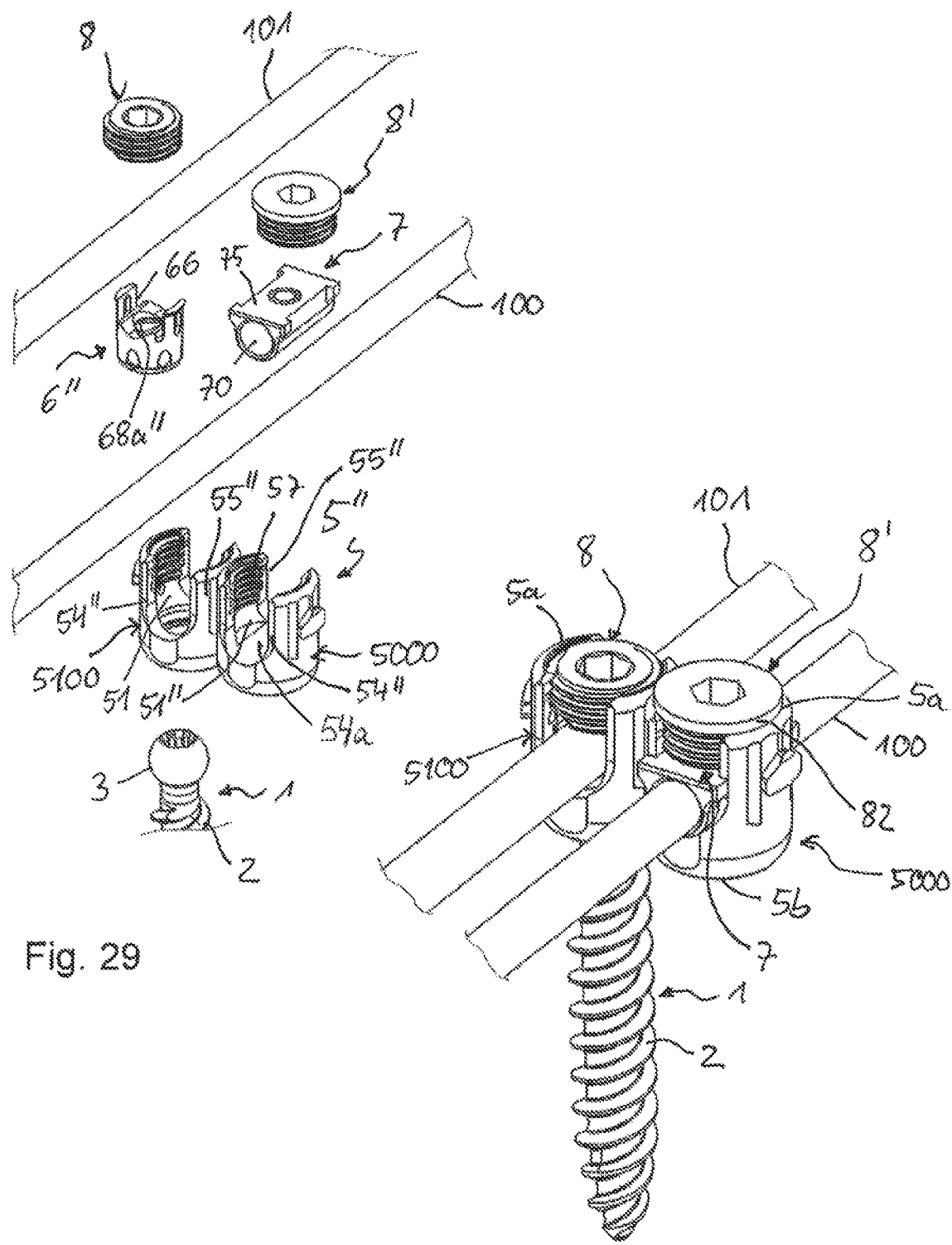
FIG. 29 shows an exploded perspective view of a still further embodiment of the bone anchoring device.
FIG. 30 shows a perspective view of the bone anchoring device of FIG. 29 in an assembled state.

Referring to FIGS. 29 and 30, a still further embodiment will be described. The descriptions of parts and portions that are identical or similar to those of the previous embodiments will not be repeated. In some applications, the use of two rods may be advantageous. In such an anchoring device, a first rod 100 may be offset from the anchoring element 1, which opens various additional options for correction.

The receiving part 5" in this embodiment is a double connecting receiving part that includes a first receiving part 5000 that is fixedly connected, preferably formed monolithically with, a second receiving part 5100, such that their top ends 5a are oriented to the same side and their rod channels, i.e., substantially U-shaped recesses 54", are aligned such that inserted rods 100, 101 are substantially parallel. Preferably, the receiving parts 5000, 5100 are connected directly at one of their legs 55" to each other. However, it may also be contemplated that they are connected via a connection portion, such that the connected legs are arranged at a distance from each other. An upper portion of the receiving part 5000 of the double connecting receiving part 5" is similar to the receiving part 5 of FIGS. 1 to 25. However, the size of the rod receiving member 7 and the rod channel are adapted to each other, such that the rod receiving member 7 with the rod 100 can be inserted directly into the U-shaped recess 54" and rests on the bottom 54a thereof. In a lower part, the receiving part 5000 may be different in that it lacks an accommodation space 53 for a head 3 of a bone anchoring element 1. In greater detail, the receiving part 5000 may be closed at the bottom end 5b. The passage 51" ends within the U-shaped recess 54". Hence, the receiving part 5000 also lacks the pressure element. The receiving part 5100 is also substantially identical or similar to the receiving part 5 of FIGS. 1 to 25, and serves to receive the head 3 of the bone anchoring element 1 and the second rod 101. A slightly modified pressure element 6" may be used for exerting pressure onto the head 3 and for receiving the second rod 101 directly in the recess 66". The recess 66" may optionally have a substantially V-shaped base 68a" for selectively receiving rods 101 of different diameters.

In one example of use, the receiving part 5000 may be used with the sliding first rod 100, for example, by inserting the second fixation member 8' that has the flange 82 and the other receiving part 5100 may be used with the second rod 101, wherein the head and the rod 101 may be fixed relative to the receiving part 5100, for example, with the first fixation member 8.

Various other embodiments including a double connecting receiving part may be contemplated, for example, the receiving part 5100 may also be provided with the rod receiving member, so that two sliding rods may be employed. With the selection of a suitable fixation member, one or both rods can be fixed.

Further modifications of the above described embodiments are also conceivable without departing from the spirit and scope of the invention. For example, the fixation member can also be a two-part fixation member, with an outer member and an inner member, wherein the outer member cooperates with the legs of the receiving part and is configured to act onto the pressure element and the inner member is configured to act on the rod receiving member. Hence, the function of the first and the third fixation members can be combined. The receiving part and the pressure element are also not limited to the detailed shapes shown. The receiving part and/or the pressure element may also have a two-part design. In an embodiment, the receiving part may also be connected monoaxially to the shank.

Moreover, the rod receiving member may also be a two-part member, wherein the lower portion can be inserted into the receiving part before the rod is placed therein, and an upper portion can be inserted once the rod has been placed into the channel.

For the bone anchoring element, all types of bone anchoring elements that are suitable for anchoring in bone or vertebra may be used, in particular also bone nails.

The rod may have various shaped and/or varying cross-sections along its length, and the passage of the rod receiving member may also have various other shapes.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for anchoring a rod to a bone or vertebra via a bone anchoring element, the bone anchoring device comprising:
   a receiving part connectable to the bone anchoring element, the receiving part comprising two legs that define a channel for the rod; and
   a rod receiving member separable from the receiving part and positionable in the channel, the rod receiving member comprising an upper surface and a lower surface that define a longitudinally extending passage for receiving the rod;
   wherein when the rod receiving member is in the receiving part, the upper and lower surfaces are respectively configured to restrict upward and downward movement of a rod received in the passage, and the rod receiving member is adjustable from a first configuration where the passage is unobstructed and the rod is movable longitudinally through the passage, to a second configuration where an engagement surface that is integrally formed with other portions of the rod receiving member and that is movable relative to the upper and lower surfaces is advanced axially into the passage to engage the rod while a rotational orientation of the engagement surface remains constant to restrict movement of the rod in the passage.

2. The bone anchoring device of claim 1, wherein the rod receiving member is deformable to facilitate movement of the engagement surface.

3. The bone anchoring device of claim 1, wherein the rod receiving member comprises a sleeve-like portion configured to extend around and enclose a circumference of the rod.

4. The bone anchoring device of claim 1, wherein the rod receiving member comprises a flexible material.

5. The bone anchoring device of claim 4, wherein the flexible material comprises a biocompatible plastic and/or another biocompatible polymer material.

6. The bone anchoring device of claim 1, wherein the engagement surface of the rod receiving member is formed by an elastically deformable region of the upper surface.

7. The bone anchoring device of claim 1, wherein the rod receiving member further comprises an abutment surface configured to cooperate with the receiving part to restrict longitudinal movement of the rod receiving member through the channel.

8. The bone anchoring device of claim 7, wherein the abutment surface is formed on a lateral extension that extends away from the longitudinal axis of the rod receiving member.

9. The bone anchoring device of claim 1, further comprising a pressure element movable in the receiving part to exert pressure onto an inserted head of a bone anchoring element.

10. The bone anchoring device of claim 9, wherein the pressure element defines a recess that forms two legs, and wherein the rod receiving member is positionable at least partially between the legs of the pressure element.

11. The bone anchoring device of claim 1, further comprising the bone anchoring element comprising a shank for anchoring in the bone or vertebra and a head.

12. The bone anchoring device of claim 11, further comprising a fixation member engageable with the legs of the receiving part to hold the head of the bone anchoring element and the rod in the receiving part.

13. The bone anchoring device of claim 12, wherein the fixation member is configured to lock a position of the head relative to the receiving part while the rod remains movable relative to the rod receiving member.

14. The bone anchoring device of claim 12, wherein advancement of the fixation member relative to the receiving part is limited by a stop, at which point the head and the rod are held in but remain movable relative to the receiving part.

15. The bone anchoring device of claim 12, wherein the fixation member comprises a projection configured to act onto the rod receiving member to adjust the rod receiving member from the first configuration to the second configuration.

16. The bone anchoring device of claim 1, further comprising the rod.

17. The bone anchoring device of claim 16, wherein the rod is inelastic.

18. The bone anchoring device of claim 1, wherein an axial height of the passage remains constant between the first configuration and the second configuration.

19. A kit comprising:
the bone anchoring device of claim 1;
the bone anchoring element comprising a shank for anchoring in the bone or vertebra and a head;
a first fixation member configured to lock the head relative to the receiving part while remaining spaced apart from the rod receiving member such that a rod that extends through the passage remains movable longitudinally relative to the receiving part; and
a second fixation member configured to exert pressure on the rod receiving member to lock both the rod and the head relative to the receiving part;
wherein the first and second fixation members are interchangeably engageable with the legs of the receiving part.

20. The kit of claim 19, further comprising a third fixation member interchangeable with the first and second fixation members to engage the legs of the receiving part, wherein advancement of the third fixation member relative to the receiving part is limited by a stop, at which point the head and the rod are held in but remain movable relative to the receiving part.

21. The kit of claim 19, wherein the second fixation member is configured to directly contact the rod receiving member to exert the pressure on the rod receiving member.

22. A method for anchoring a rod to a bone or vertebra using a bone anchoring device comprising a bone anchoring element comprising a shank for anchoring in the bone or vertebra and a head, a receiving part connectable to the head of the bone anchoring element, the receiving part comprising two legs that define a channel for the rod, a rod receiving member separable from the receiving part and positionable in the channel, the rod receiving member comprising an upper surface and a lower surface that define a longitudinally extending passage for receiving the rod, and a fixation member, the method comprising:
anchoring the shank of the bone anchoring element to bone;
adjusting an angular position of the receiving part relative to the shank when the head is in the receiving part;
inserting the rod receiving member into the channel while the rod extends through the passage, such that the upper and lower surfaces are respectively configured to restrict upward and downward movement of the rod in the passage, and the rod receiving member is adjustable from a first configuration where the passage is unobstructed and the rod is movable longitudinally through the passage, to a second configuration where an engagement surface that is integrally formed with other portions of the rod receiving member and that is movable relative to the upper and lower surfaces is advanced axially into the passage to engage the rod while a rotational orientation of the engagement surface remains constant to restrict movement of the rod in the passage;
engaging the fixation member with the legs to hold the head of the bone anchoring element and the rod in the receiving part.

23. A bone anchoring device for anchoring a rod to a bone or vertebra, the bone anchoring device comprising:
a bone anchoring element comprising a head and a shank for anchoring in the bone or vertebra;
a receiving part connectable to the bone anchoring element, the receiving part comprising two legs that define a channel for the rod;
a rod receiving member separable from the receiving part and positionable in the channel, the rod receiving member comprising an upper surface and a lower surface that define a longitudinally extending passage for receiving the rod; and
a fixation member engageable with the legs of the receiving part to hold the head of the bone anchoring element and the rod in the receiving part, wherein the fixation member is configured to lock a position of the head relative to the receiving part while the rod remains movable relative to the rod receiving member;
wherein when the rod receiving member is in the receiving part, the upper and lower surfaces are respectively configured to restrict upward and downward movement of a rod received in the passage, and the rod receiving member is adjustable from a first configuration where the passage is unobstructed and the rod is movable longitudinally through the passage, to a second configuration where an engagement surface attached to other portions of the rod receiving member is advanced axially into the passage to engage the rod while a rotational orientation of the engagement surface remains constant to restrict movement of the rod in the passage.

\* \* \* \* \*